United States Patent
Flaschenriem et al.

(10) Patent No.: US 10,212,908 B2
(45) Date of Patent: Feb. 26, 2019

(54) MALE STERILITY IN CATHARANTHUS

(71) Applicant: Ball Horticultural Company, West Chicago, IL (US)

(72) Inventors: Denis R. Flaschenriem, Santa Maria, CA (US); Alan D. Blowers, Elburn, IL (US)

(73) Assignee: BALL HORTICULTURAL COMPANY, West Chicago, IL (US)

( * ) Notice: Subject to any disclaimer, the term of this patent is extended or adjusted under 35 U.S.C. 154(b) by 10 days.

(21) Appl. No.: 15/331,419

(22) Filed: Oct. 21, 2016

(65) Prior Publication Data

US 2017/0118933 A1 May 4, 2017

Related U.S. Application Data

(60) Provisional application No. 62/248,225, filed on Oct. 29, 2015.

(51) Int. Cl.

| | | |
|---|---|---|
| *A01H 5/02* | (2018.01) | |
| *A01H 1/02* | (2006.01) | |
| *A01H 1/04* | (2006.01) | |
| *C12Q 1/68* | (2018.01) | |
| *A01H 6/08* | (2018.01) | |
| *C12Q 1/6827* | (2018.01) | |
| *C12Q 1/6895* | (2018.01) | |

(52) U.S. Cl.
CPC .............. *A01H 6/084* (2018.05); *A01H 1/04* (2013.01); *C12Q 1/6827* (2013.01); *C12Q 1/6895* (2013.01); *A01H 1/02* (2013.01); *A01H 5/02* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 6,166,306 A | 12/2000 | Bowman | |
| PP18,315 P3 * | 12/2007 | Kumar | A01H 5/02 Plt./263.1 |
| 7,642,436 B2 * | 1/2010 | Riebel | A01H 5/02 435/410 |
| 9,451,747 B2 | 7/2016 | Flaschenriem | |
| 9,451,748 B2 | 7/2016 | Flaschenriem | |
| 9,451,749 B2 | 7/2016 | Flaschenriem | |
| 9,451,750 B2 | 7/2016 | Flaschenriem | |
| 9,451,751 B2 | 7/2016 | Flaschenriem | |
| 9,451,752 B2 | 7/2016 | Flaschenriem | |

OTHER PUBLICATIONS

Sreevalli et al. Indian Journal of Genetics 63(4): 365-366 (2003).*
Wang et al. BMC Biotechnology 12(34): 1-12 (2012).*
Junaid et al. Plant Growth Regulation 51(3): 271-281 (2007).*
Goldsmith Seeds, "Cora™ Vinca by Goldsmith," available on the Internet at <https://parksbros.files.wordpress.com/2008/09/all-about-cora-vinca.pdf>, dated Jul. 15, 2008.

* cited by examiner

*Primary Examiner* — David T Fox
(74) *Attorney, Agent, or Firm* — Dentons US LLP

(57) ABSTRACT

The invention provides *Catharanthus* plants comprising a male sterility allele and methods for producing a plant produced by crossing such plants with themselves or with another plant, such as a plant of another genotype. The invention further relates to seeds and plants produced by crossing *Catharanthus* plants comprising a male sterility allele. The invention further relates to parts of such plants.

31 Claims, 2 Drawing Sheets
Specification includes a Sequence Listing.

MALE STERILITY IN CATHARANTHUS

CROSS REFERENCE TO RELATED APPLICATIONS

This application claims the priority of U.S. Provisional Appl. Ser. No. 62/248,225, filed Oct. 29, 2015, the entire disclosure of which is incorporated herein by reference.

FIELD OF THE INVENTION

The present invention relates to the field of plant breeding and, more specifically, to the development of male sterile *Catharanthus* plants and seeds and hybrids thereof.

INCORPORATION OF SEQUENCE LISTING

The sequence listing contained in the file named "BALL032US_ST25.txt", which is 1.26 kilobytes (size as measured in Microsoft Windows®) and was created on Oct. 21, 2016, is filed herewith by electronic submission and is incorporated by reference herein.

BACKGROUND OF THE INVENTION

Male sterility is a condition in which functional anthers, pollen, or male gametes are not produced, while female reproduction remains functional. The present invention relates to genic male sterility caused by a nuclear gene. Male-sterile mutations provide genetic material for breeding novel hybrid *Catharanthus* varieties.

SUMMARY OF THE INVENTION

In one aspect, the invention provides a *Catharanthus* plant comprising a nuclear recessive allele that confers male sterility to the plant, wherein a representative deposit of seed comprising said allele has been deposited under ATCC Accession No. PTA-122493. In some embodiments, the plant is homozygous for the allele, or is heterozygous for the allele. In other embodiments, the plant is hybrid or is inbred. In still other embodiments, the plant comprises a transgene, or comprises a single locus conversion. In another embodiment, the invention provides a plant part comprising a cell of a *Catharanthus* plant comprising a nuclear recessive allele that confers male sterility to the plant, such as a cutting, a leaf, pollen, an ovule, or a flower. In some embodiments, the invention provides a seed that produces such a plant, or a seed produced from such a plant. In still other embodiments, such a seed is inbred or is hybrid. In another embodiment, the invention provides a tissue culture of regenerable cells of such a plant. In another embodiment, such a tissue culture comprises cells or protoplasts from a plant part selected from the group consisting of embryos, meristems, cotyledons, pollen, leaves, anthers, roots, root tips, pistil, flower, seed, stems, and protoplasts or callus derived therefrom. In another embodiment, the invention provides a plant regenerated from such a tissue culture, wherein the regenerated plant comprises the male sterility allele. In another embodiment, the invention provides a method of producing a plant comprising an added desired trait, the method comprising introducing a transgene or single locus conversion conferring the desired trait into a *Catharanthus* plant comprising a nuclear recessive allele that confers male sterility to the plant.

In another aspect, the invention provides a method of introducing a desired trait into a plant comprising: (a) crossing a *Catharanthus* plant comprising a nuclear recessive allele that confers male sterility to the plant with a second, distinct plant that comprises a desired trait to produce F1 progeny; (b) selecting an F1 progeny that comprises the desired trait; (c) crossing the selected F1 progeny with a plant of the same variety as a *Catharanthus* plant comprising a nuclear recessive allele that confers male sterility to the plant, wherein the plant is homozygous for the allele, to produce backcross progeny; and (d) repeating steps (c) and (d) three or more times in succession to produce selected fourth or higher backcross progeny that comprise the desired trait. In one embodiment, the plant comprises said male sterility allele.

In another aspect, the invention provides a method for producing hybrid *Catharanthus* seed comprising the steps of: (a) crossing a *Catharanthus* plant comprising a nuclear recessive allele that confers male sterility to the plant, wherein a representative deposit of seed comprising said allele has been deposited under ATCC Accession No. PTA-122493, and wherein the plant is homozygous for the allele, with a second, distinct plant capable of being crossed thereto; and (b) collecting resulting seed. In one embodiment, the method further comprises the steps of: (c) crossing a plant grown from said seed of step (b) with itself or a different plant at least one additional time to yield additional seed. In one embodiment, such a plant is a *Catharanthus* seed. In another embodiment, the *Catharanthus* plant is a *Catharanthus roseus* plant comprising said allele, wherein a representative deposit of seed comprising said allele has been deposited under ATCC Accession No. PTA-122493. In another embodiment, the *Catharanthus roseus* plant is a plant of *Catharanthus* line H7487D, P7998D, or P6485D.

In another aspect, the invention provides a method of producing a *Catharanthus* plant with an allele that confers male sterility, said method comprising introgressing the allele from a *Catharanthus* plant comprising a nuclear recessive allele that confers male sterility to the plant into a plant of a different genotype. In some embodiments, the invention provides an F1 hybrid seed having as one parent a *Catharanthus* plant comprising a nuclear recessive allele that confers male sterility to the plant, wherein a representative deposit of seed comprising said allele has been deposited under ATCC Accession No. PTA-122493. In one embodiment, said plant is used as the female parent. In another embodiment, the invention provides a plant produced by growing an F1 hybrid seed having as one parent a *Catharanthus* plant comprising a nuclear recessive allele that confers male sterility to the plant, wherein the plant comprises the allele. In an embodiment, said plant is a female parent. In another embodiment, the invention provides a plant part comprising a cell of such a plant, such as a cutting, leaf, an ovule, pollen, or a flower.

In another aspect, the invention provides a method of vegetatively propagating a *Catharanthus* plant comprising a nuclear recessive allele that confers male sterility to the plant comprising the steps of: (a) collecting tissue capable of being propagated from such a *Catharanthus* plant; (b) cultivating said tissue to obtain proliferated shoots; and (c) rooting said proliferated shoots to obtain rooted plantlets. In one embodiment, the method further comprises growing at least a first plant from said rooted plantlets.

In another aspect, the invention provides a hybrid *Catharanthus* plant comprising a nuclear recessive allele conferring male sterility, obtainable by crossing a *Catharanthus* plant comprising said allele, with a second plant lacking said allele, wherein a representative deposit of seed comprising said allele has been deposited under ATCC Accession No.

PTA-122493. In one embodiment, the *Catharanthus* plant comprising the nuclear recessive allele is used as the female parent.

DETAILED DESCRIPTION OF THE INVENTION

Figure 1:
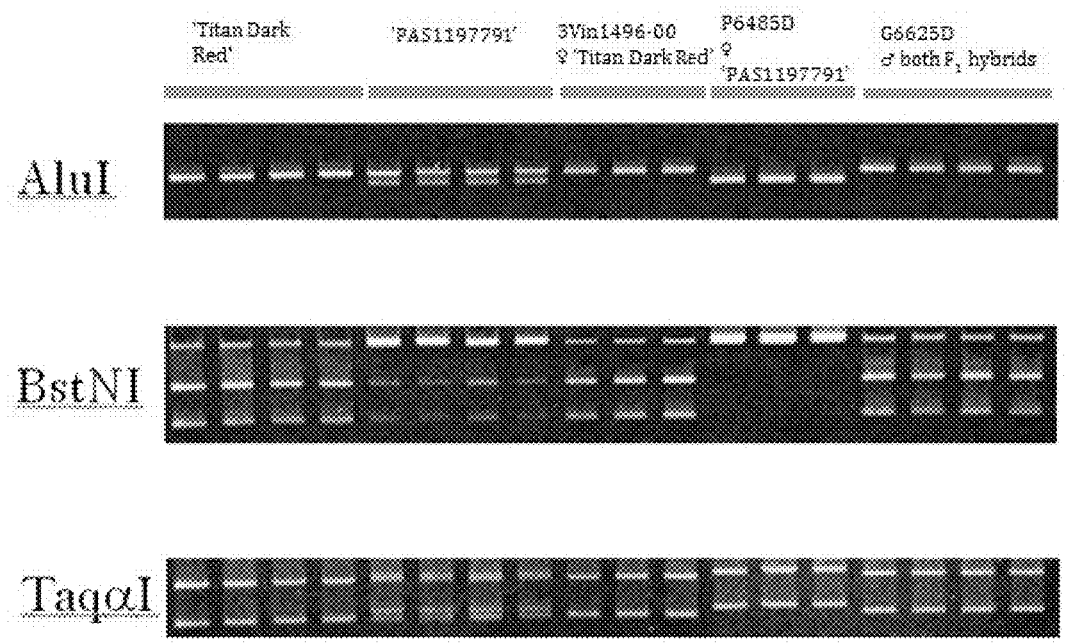
FIG. 1—Shows CAPS marker assays to differentiate *Vinca* varieties 'Titan Dark Red' and 'PAS1197791'.

The invention provides male sterile *Catharanthus* plants, plant parts, seeds, and progeny plants containing a nuclear recessive male sterility allele as described herein. The invention also provides methods for producing *Catharanthus* hybrid seed and plants.

*Catharanthus* flowers are perfect, having both male and female organs in the same flower, and as a result, reproduction occurs naturally through self-pollination. Many agricultural and horticultural crops are grown from F1 seed, and sold commercially as F1 hybrid plants. Production of F1 hybrids may be utilized as an alternative to selfing, and thus prevention of self-pollination is key to producing F1 hybrid seed. During F1 hybrid seed production, pollen from an inbred "male" *Catharanthus* line is used to pollinate a different inbred "female" line. F1 hybrids resulting from crosses of selfed parental lines exhibit uniform morphological and physiological traits and tend to be more vigorous and thus more commercially valuable than inbred lines.

Various methods may be employed to prevent selfing in a plant line to be used as a female parent. For example, emasculation may be done by manually removing the anthers of a plant before pollen is available for self-pollination. Although commonly employed in numerous crops, emasculation is expensive and time-consuming, requiring considerable effort to ensure that all anthers are removed. Additionally, the small size of the flower parts in *Catharanthus* plants renders it unsuitable for emasculation on a commercial scale. Other methods utilized for prevention of self-pollination include application of chemical agents that suppress pollen production in a plant, although the costs associated with these chemicals is often prohibitive for ornamental crops. Male sterility (MS), both naturally occurring and artificially induced, may also be used to prevent self-pollination in plants. Male sterility in plants results when production of male gametes is inhibited or prevented such that pollen is not produced, although female reproduction remains functional.

As described herein, the present invention provides male sterile *Catharanthus* plants, plant parts, seeds, and progeny plants containing a nuclear recessive male sterility allele, whereby such plants may be used as a female breeding parent. Methods for producing such *Catharanthus* plants and seeds are also provided. Male sterility as described herein is the result of a nuclear male sterility gene or allele and is inherited in a recessive manner, thereby enabling predictable transmission of the trait to progeny plants. In accordance with the invention, a parent line homozygous for an allele producing male sterility will transmit the allele to all of its progeny, resulting in F1 hybrids that carry but do not express the male sterility trait.

A. Breeding *Catharanthus* Plants Comprising a Male Sterility Allele

The development of new varieties using one or more starting varieties is well known in the art and encompassed by the present invention. In accordance with the invention, novel *Catharanthus* varieties may be created by crossing a plant of the invention followed by multiple generations of breeding according to such well-known methods. New varieties with the disclosed male sterility trait or allele may be created by crossing with any second plant.

In selecting a second plant to cross with a plant of the invention, it will typically be preferred to choose those plants which either themselves exhibit one or more selected desirable characteristics or which exhibit the desired characteristic(s) when in hybrid combination. Once initial crosses have been made, selection takes place to produce new varieties. Examples of desirable traits may include, in specific embodiments, male sterility, flower color or size, color patterning, foliage quality, shape and uniformity, maturity date, flower yield, seed germination rate, seedling vigor, disease tolerance or resistance, and adaptability for soil and climate conditions. Consumer-driven traits are other traits that may be incorporated into new plants developed by this invention.

One aspect of the current invention provides methods for producing a plant with a male sterility allele. In certain embodiments, such a method may comprise: (a) crossing a *Catharanthus* plant comprising an allele that confers to the plant male sterility with a second plant that comprises at least a first desired trait to produce F1 progeny; (b) selecting an F1 progeny that comprises a male sterility allele and any additional desired trait(s); (c) crossing the selected F1 progeny with itself or another *Catharanthus* plant; and (d) repeating steps (c) and (d) three or more times in succession to produce selected fourth or higher generation progeny that comprise the male sterility allele and one or more desired trait(s). In a particular embodiment, the second plant may be a *Catharanthus* plant and the progeny seed may be planted and grown to produce fertile hybrid progeny plants. In some embodiments, a plant of the invention may be homozygous for the recessive male sterility allele and therefore exhibit the male sterility trait. In other embodiments, a *Catharanthus* plant as described herein may comprise a single male sterility allele and therefore be referred to as a fertile hybrid *Catharanthus* plant. A male-sterile plant in accordance with one embodiment of the invention may be used in such crosses as the female plant. In some embodiments, selection of a plant comprising a male sterility trait may involve evaluation of the flowers of the plant for pollen production. One of skill in the art will understand the transmission of a recessive trait such as male sterility in accordance with the invention.

Some embodiments of the current invention provide methods for producing seed of a *Catharanthus* hybrid such as 'PAS1157216' or 'PAS1197791' involving crosses with female *Catharanthus* parental lines P7998D and P6485D, respectively, as described in detail in the Examples. Alternatively, in other embodiments of the invention, a plant of a hybrid variety and a parental line described herein may be crossed with itself or with any second plant. Such methods can be used for propagation of a hybrid and/or a *Catharanthus* parental line described herein, or can be used to produce plants that are derived from such a hybrid and/or a *Catharanthus* parental line. Plants derived from a hybrid and/or a *Catharanthus* parental line as described herein may be used, in certain embodiments, for the development of new *Catharanthus* varieties comprising a male sterility allele.

The invention also provides methods of producing *Catharanthus* plants comprising (a) crossing a *Catharanthus* plant comprising a male sterility allele as described herein with itself or a second plant capable of being crossed thereto; and (b) collecting resulting seed. In embodiments of the invention, the first *Catharanthus* plant is homozygous for the male sterility allele. In one embodiment, the second plant may be a *Catharanthus* plant. In some embodiments, the methods of the present invention may further comprise the step of (c) crossing a plant grown from said seed of step (b) with itself or a second plant at least one or more additional time(s) to yield additional seed. Plants, seeds, and plant parts produced from the methods described herein and which comprise a male sterility allele as described herein are also provided.

In certain embodiments, hybrid seeds may be produced using the methods of the present invention. A parent plant of such a seed may be a *Catharanthus* plant comprising a male sterility allele that confers male sterility to the plant. In some embodiments, the parent plant may be homozygous or heterozygous for the male sterility allele. In other embodiments, a plant as described herein may be the female plant in a given cross.

In accordance with the invention, any species of *Catharanthus* may be used. In particular, *Catharanthus* species that may be useful include, but are not limited to, *Catharanthus* roseus, *Catharanthus coriaceus, Catharanthus lanceus, Catharanthus longifollus, Catharanthus ovalis, Catharanthus* pusillus, *Catharanthus scitulus, Catharanthus trichophyllus*, and the like.

In certain other embodiments, a plant of the invention may be an inbred plant, or may be a hybrid plant, such as an F1 hybrid. In addition, a plant of the present invention may be homozygous for a male sterility allele that confers male sterility to the plant or a plant of the invention may be heterozygous for the allele.

In further embodiments, the present invention provides plants modified using the methods described herein to include at least a first desired heritable trait. Such plants may, in one embodiment, be developed by backcrossing, wherein essentially all of the desired morphological and physiological characteristics of a variety are recovered in addition to a genetic locus transferred into the plant via the backcrossing technique. The term single locus converted plant as used herein refers to those plants which are developed by backcrossing, wherein essentially all of the desired morphological and physiological characteristics of a variety are recovered in addition to the single locus transferred into the variety via the backcrossing technique. By essentially all of the desired morphological and physiological characteristics, it is meant that the characteristics of a plant are recovered that are otherwise present when compared in the same environment, other than an occasional variant trait that might arise during backcrossing or direct introduction of a transgene.

Backcrossing can be used to improve a variety, and may be used, for example, to introduce a male sterility allele into the plant genetic background of any plant that is sexually compatible with *Catharanthus*, as well as to introduce one or more traits into a plant of the invention. Backcrossing transfers a specific desired trait from one inbred or non-inbred source to a variety that lacks that trait. This can be accomplished, for example, by first crossing a variety of a desired genetic background (recurrent parent) to a donor inbred (non-recurrent parent), which carries the appropriate allele or loci for the desired trait(s) in question. The progeny of this cross are then mated back to the recurrent parent, followed by selection in the resultant progeny for the desired trait to be transferred from the non-recurrent parent. The process is repeated, for example for five or more backcross generations with selection for the desired trait, until a plant is obtained wherein essentially all of the desired morphological and physiological characteristics of the recurrent parent are recovered in the converted plant, in addition to the single transferred locus from the nonrecurrent parent. The progeny thus have the characteristic being transferred, but are like the superior parent for most or almost all other loci. The last backcross generation can be selfed to give true-breeding progeny when the trait being transferred is introgressed into a true-breeding variety.

The recurrent parent therefore provides the desired genetic background, while the choice of the particular non-recurrent parent will depend on the purpose of the backcross. One of the major purposes is to add some commercially desirable trait to the plant. The exact backcrossing protocol will depend on the characteristic or trait being altered and the genetic distance between the recurrent and nonrecurrent parents. Although backcross sing methods are simplified when the characteristic being transferred is a dominant allele, a recessive allele or an additive allele (between recessive and dominant) may also be transferred. In this instance it may be necessary to introduce a test of the progeny to determine if the desired characteristic has been successfully transferred.

Modified backcrossing may also be used with plants comprising a male sterility trait or allele. This technique uses different recurrent parents during the backcrossing. Modified backcrossing may be used to replace the original recurrent parent with a variety having certain more desirable characteristics or multiple parents may be used to obtain different desirable characteristics from each.

B. Further Embodiments of the Invention

In other embodiments, the invention provides methods of vegetatively propagating a *Catharanthus* plant of the invention. Such a method may comprise methods known in the art, such as tissue culture. For example, vegetative propagation of a plant of the invention may comprise the steps of: comprising the steps of: (a) collecting tissue capable of being propagated from said plant; (b) cultivating said tissue to obtain proliferated shoots; and (c) rooting said proliferated shoots to obtain rooted plantlets. In other embodiments, such a method may further comprise growing *Catharanthus* plants from the rooted plantlets. In still further embodiments, a plant of the invention is propagated by seed, wherein a plant comprising a male sterility allele may be used as a female parent for producing progeny seed and plants.

Also provided are methods of producing a *Catharanthus* plant with a male sterility allele that confers male sterility, said method comprising introgressing the male sterility allele from a plant comprising such an allele into a plant of a different genotype. In certain embodiments, the male sterility allele may be inherited from a *Catharanthus* variety described herein comprising a male sterility allele or a progeny of any generation thereof comprising the allele.

Many single locus traits have been identified that are not regularly selected for in the development of a new inbred but that can be improved by backcrossing techniques. Single locus traits may or may not be transgenic; examples of these traits include, but are not limited to, resistance to bacterial, fungal, or viral disease, or herbicide or insect resistance. These comprise genes generally inherited through the nucleus.

Direct selection may be applied where the single locus acts as a dominant trait. For this selection process, the progeny of the initial cross are assayed for the desired trait and/or the presence of the corresponding gene prior to the backcrossing. Selection eliminates any plants that do not have the desired gene and/or trait, and only those plants that have the trait are used in the subsequent backcross. This process is then repeated for all additional backcross generations.

Selection of *Catharanthus* plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker-assisted selection. Any other type of genetic marker or other assay which is able to identify the relative presence or absence of a trait of interest in a plant can also be useful for breeding purposes. Procedures for marker assisted selection are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

C. Plants Derived by Genetic Engineering

Many useful traits that can be introduced by backcrossing, as well as directly into a plant, are those which are introduced by genetic transformation techniques. Genetic transformation may therefore be used to insert a selected transgene or single locus conversion into a plant of the invention or may, alternatively, be used for the preparation of transgenes or single locus conversions that can be introduced by backcrossing. Methods for the transformation of plants that are well known to those of skill in the art and applicable to many crop species include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly using tissue culture methods known in the art. In this technique, one would partially degrade the cell walls of the chosen cells by exposing them to pectin-degrading enzymes (pectolyases) or mechanically wound tissues in a controlled manner.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994), and Ellul et al. (2003).

A number of promoters have utility for plant gene expression for any gene of interest including but not limited to selectable markers, scoreable markers, genes for pest tolerance, disease resistance, and any other gene of agronomic interest. Examples of constitutive promoters useful for driving gene expression in plants include, but are not limited to, the cauliflower mosaic virus (CaMV) P-35S promoter, which confers constitutive, high-level expression in most plant tissues (see, e.g., Odel et al., 1985), including monocots (see, e.g., Dekeyser et al., 1990; Terada and Shimamoto, 1990); a tandemly duplicated version of the CaMV 35S promoter, the enhanced 35S promoter (P-e35S) the nopaline synthase promoter (An et al., 1988), the octopine synthase promoter (Fromm et al., 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a *commelina* yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wunl, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989).

Exemplary nucleic acids which may be introduced to the plants of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a plant comprising a male sterility allele according to the invention. Non-limiting examples of particular genes and corresponding phenotypes one may choose to introduce into a of the invention include one or more genes for insect tolerance, pest tolerance, such as genes for fungal disease control, herbicide tolerance such as genes conferring glyphosate tolerance, and genes for quality improvements such as environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (i.e., a ribozyme) engineered to cleave a desired endogenous mRNA product (see, for example, Gibson and Shillito, 1997). Thus, any gene which produces a protein or mRNA which expresses a phenotype or morphology change of interest is useful for the practice of the present invention.

D. Definitions

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid (F1), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor or a chemical agent conferring male sterility.

Enzymes: Molecules which can act as catalysts in biological reactions.

F1 Hybrid: The first generation progeny of the cross of two non-isogenic plants.

Genotype: The genetic constitution of a cell or organism.

Haploid: A cell or organism having one set of the two sets of chromosomes in a diploid.

Hybrid: F1 progeny produced from crossing two non-identical parental lines. Parental lines may be related or unrelated. In accordance with the present invention, a "hybrid" may refer to *Catharanthus* plants comprising a male sterility allele as described herein.

Inbred Line: A group of genetically and phenotypically similar plants reproduced by inbreeding.

Linkage: A phenomenon wherein alleles on the same chromosome tend to segregate together more often than expected by chance if their transmission was independent.

Phenotype: The detectable characteristics of a cell or organism, which characteristics are the manifestation of gene expression.

Plant Part: As used herein, a plant part refers to a part of a plant of the present invention. A plant part may be defined as comprising a cell of such plant, such as a cutting, a leaf, a floret, an ovule, pollen, a cell, a seed, a flower, an embryo, a meristem, a cotyledon, an anther, a root, a root tip, a pistil, a stalk, a stem, and a protoplast or callus derived therefrom.

Quantitative Trait Loci (QTL): Quantitative trait loci (QTL) refer to genetic loci that control to some degree numerically representable traits that are usually continuously distributed.

Regeneration: The development of a plant from tissue culture. In accordance with the invention, a regenerated *Catharanthus* plant as described herein would comprise a male sterility allele that confers male sterility.

Self-pollination or self-fertilization: The transfer of pollen from the anther to the stigma of the same plant. A "self-pollinated" or "self-fertilized" seed refers to a seed arising from fusion of male and female gametes produced by the same plant. In hybrid seed production, self-pollinated or self-fertilized seed refers to that portion (e.g., less than 1%) of the seed that was the result of self-pollination.

Single Locus Converted (Conversion) Plant: Plants which are developed by a plant breeding technique called backcrossing, wherein essentially all of the desired morphological and physiological characteristics of a *Catharanthus* variety are recovered in addition to the characteristics of the single locus transferred into the variety via the backcrossing technique and/or by genetic transformation.

Substantially Equivalent: A characteristic that, when compared, does not show a statistically significant difference (e.g., p=0.05) from the mean.

Tissue Culture: A composition comprising isolated cells of the same or a different type or a collection of such cells organized into parts of a plant. A tissue culture in accordance with the invention may originate from or comprise cells or protoplasts from a plant part selected from the group consisting of embryos, meristems, cotyledons, pollen, leaves, anthers, roots, root tips, pistil, flower, florets, seed, stems, and protoplasts or callus derived therefrom.

E. Deposit Information

A deposit of *Catharanthus* line P7998D, disclosed above and recited in the claims, has been made with the American Type Culture Collection (ATCC), 10801 University Blvd., Manassas, Va. 20110-2209. The date of the deposit was Sep. 3, 2015. The accession number for those deposited seeds of *Catharanthus* line P7998D is ATCC Accession Number PTA-122493. Upon issuance of a patent, all restrictions upon the deposits will be removed, and the deposits are intended to meet all of the requirements of 37 C.F.R. § 1.801-1.809. The deposits will be maintained in the depository for a period of 30 years, or 5 years after the last request, or for the effective life of the patent, whichever is longer, and will be replaced if necessary during that period.

EXAMPLES

Although the foregoing invention has been described in some detail by way of illustration and example for purposes of clarity and understanding, it will be obvious that certain changes and modifications may be practiced within the scope of the invention, as limited only by the scope of the appended claims.

Example 1

Origin and Breeding History of *Catharanthus* Inbred Male-Sterile Line

Two thousand seeds of Ball Horticultural Company proprietary *Catharanthus roseus* inbred line F6211D were treated with 0.40% (v/v) ethyl methanesulfonate (EMS) (Sigma-Aldrich Cat. No. M0880) with constant stirring for 12 hours at room temperature. Following EMS treatment, the seeds were washed with distilled water by stirring for four hours, with wash changes every 15 minutes. The mutagenized seed was sown and the M1 population grown to sexual maturity. Flowering M1 plants were self-pollinated and M2 seed harvested from approximately 1,500 M1 plants. The M2 seed from ten M1 plants was bulked together into a single seed lot, creating approximately 150 lots of M2 seed. The M2 seed was sown (approximately 20 seeds per M1 plant or approximately 200 seeds per M2 seed lot) and grown to the flowering stage to observe male reproductive development in the 30,000 M2 plant population.

From the 30,000 plants screened, 81 male-sterile (MS) plants were identified based on a lack of pollen production. These plants were transplanted to larger containers and monitored for stability of the MS trait. Some of the plants were completely sterile, while others reverted back to the fertile condition. Three stable MS plants were identified and crossed to the source inbred line F6211D. Three F1 plants selected from the progeny were sown in a greenhouse, and the resulting plants were massed to produce F2 seed. The F2 seed was sown, and from the progeny plants, the number of MS and normal flowers were recorded. The F2 family segregated MS to fertile in a 1:1 ratio, indicating that MS was inherited in the population as a single recessive genetic factor. The plants from this family were massed and assigned inbred line H7487D. Massed seed from H7487D was sown in a greenhouse. The H7487D line was stable and maintained a 1:1 segregation ratio for MS.

Line H7487D was crossed to *Catharanthus roseus* varieties 'Cora White' and 'Cora Punch' to confirm the novelty of the H7487D male-sterility trait. The resulting F1 seed was sown, and all resulting F1 plants were observed to be male-fertile, confirming a separate and novel source of male sterility.

Line H7487D was also crossed to Ball Horticultural Company proprietary inbred lines D7509D and F6211D, and F1 progeny were backcrossed to line H7487D. The resulting progeny plants were evaluated and found to segregate 1:1 for MS to fertile, confirming single recessive inheritance.

Example 2

Introgression of *Catharanthus* Male Sterility into Female Inbred Breeding Lines to Produce Female Inbred Line P7998D The male-sterility trait from inbred line H7487D was introgressed into additional inbred lines for use in a breeding program. Line H7487D was crossed to *Catharanthus roseus* 'Pacifica Really Red' (U.S. PVP No. 200600190). The F1 seed was sown in a greenhouse, and the resulting plants were massed to produce F2 seed. The F2 seed was sown and the resulting plants were evaluated for MS and normal flower development. Multiple male-fertile single plant selections with red petals were self-pollinated. The F3 seed was sown, and the resulting F3 populations were evaluated in the greenhouse. The F3 families segregated for MS, and an individual MS plant characterized by its red petal color and light-colored orifice was selected and coded 09-966-04 ms.

The selection 09-966-04 ms was crossed to 'Pacifica Really Red', and F1 seed was sown in a greenhouse. The resulting plants were massed to produce F2 seed. The resulting F2 plants were evaluated, and single plant selections were made for general horticultural characteristics, including well-branched habit, early flowering, large red flowers with light-colored orifice, and overlapping petals.

Several F3 families segregating 3 fertile:1 sterile were selected. Plants having the characteristics described above were sib-crossed with male-fertile plants having similar characteristics in order to ensure that male sterility would be maintained at a 1:1 ratio in the following generation.

Subsequent F4 and F5 generations were advanced while continuing to select for families with the most uniform previously described characteristics. One of the F5 families was massed to produce breeder's seed. The massed seed was used to make stock seed.

The plants massed were uniform and stable. No variants or off-types were observed in either the breeder's seed increase or the stock seed increase. The male sterility trait segregated 1:1 from both masses. The inbred line was designated P7998D. Inbred line P7998D was stable for two generations of seed increase, which include the breeder's seed increase and the stock seed increase.

Example 3

Introgression of *Catharanthus* Male Sterility into Female Inbred Breeding Lines to Produce Female Inbred Line P6485D Inbred line H7487D was crossed to Ball Horticultural Company proprietary inbred line 08-168 characterized by its red-colored flowers with a dark-colored orifice. The F1 seed was sown in a greenhouse, and the resulting plants were massed to produce F2 seed. The F2 plants were evaluated. Multiple male-fertile single plant selections having red-colored flowers with a dark-colored orifice were self-pollinated. The resulting F3 populations were evaluated in the greenhouse. The F3 families segregated for MS, and an individual MS plant characterized by its red petals and dark-colored orifice was selected and coded 09-959-01 ms.

The selection 09-959-01 ms was crossed to Ball Horticultural Company proprietary inbred line 09-304 characterized by its red-color flowers with a dark-colored orifice. The F1 seed was sown in a greenhouse, and the resulting plants were massed to produce F2 seed. The resulting F2 plants were evaluated, and single plant selections were made for general horticultural characters, including well-branched habit, early flowering, large red-colored flowers having a dark-colored orifice, and overlapping petals.

Several F3 families segregating in a 3 fertile:1 sterile were selected. Plants having the characteristics described above were sib-crossed with male-fertile plants of similar characteristics to ensure that male sterility would be maintained at a 1:1 ratio in the following generation.

Subsequent F4 and F5 generations were advanced while continuing to select for families with the most uniform previously described characteristics. One of the F5 families was massed to produce breeder's seed. The massed seed was used to make stock seed.

The plants massed were uniform and stable. No variants or off-types were observed in either the breeder's seed increase or the stock seed increase. Male sterility segregated 1:1 from both masses. The inbred line was designated P6485D. Inbred line P6485D was stable for two generations of seed increase, which include the breeder's seed increase and the stock seed increase.

Example 4

Origin and Breeding History of *Catharanthus* Hybrid 'PAS1157216'

*Catharanthus* hybrid variety 'PAS1157216' originated from a cross made in a greenhouse located in Guadalupe, Calif. Ball Horticultural Company proprietary inbred line P7998D described above was used as the female parent, and 'Pacifica Really Red' was used as the male parent. The hybrid was trialed in California, Illinois, and Florida. The hybrid was evaluated for desired horticultural characteristics, including habit and flower color at all the above trial locations, all of which were found to be uniform and stable.

A small production test was conducted in Guatemala to evaluate seed yield and seed quality of the hybrid. Seed from this production test was sent to research stations in California, Illinois, and Florida for evaluation. A larger production test was conducted in Guatemala to evaluate seed yield and quality of the hybrid. Seed from the production test was sent to research stations in California, Illinois, and Florida. The hybrid was designated variety 'PAS1157216' and has shown uniformity and stability, as described in the variety description information. Physiological and morphological characteristics for hybrid 'PAS1157216' and parent line P7998D are provided in Tables 1 and 2, respectively. Color chart references provided herein are to the Pantone Color Bridge, 2$^{nd}$ Edition (Pantone LLC, Carlstadt, N.J.).

TABLE 1

Physiological and Morphological Characteristics of Hybrid 'PAS1157216'

| | 'PAS1157216' | 'Cora Red' |
|---|---|---|
| 1. OVERALL PLANT HABIT (at flowering stage): | | |
| Species: 1 = *C. roseus*; 2 = Other | 1 | 1 |
| Ploidy: 1 = Haploid; 2 = Diploid; 3 = Triploid; 4 = Tetraploid | 2 | 2 |
| Life Cycle: 1 = Annual; 2 = Biennial; 3 = Perennial | 1 | 1 |
| Growth Habit: 1 = Determinate; 2 = Semi-determinate; 3 = Indeterminate | 2 | 2 |
| Growth Form: 1 = Upright; 2 = Semi-prostrate; 3 = Prostrate | 1 | 1 |
| Flowering: 1 = Very Early; 2 = Early; 3 = Mid-season; 4 = Late; 5 = Continuous | 2 | 2 |
| Days from Planting to 50% Flowering | 49 | 53 |
| Length of Flowering Season in Days | until frost | until frost |
| Plant Height at Maturity (cm) | 32 | 37 |
| Plant Width at Maturity (cm) | 32 | 30 |
| Plant Height Class: 1 = Extra Dwarf; 2 = Dwarf; 3 = Semi-dwarf; 4 = Tall | 2 | 2 |
| Plant Width Class: 1 = Compact; 2 = Semi-compact; 3 = Spreading/Lax | 1 | 1 |

TABLE 1-continued

Physiological and Morphological Characteristics of Hybrid 'PAS1157216'

|  | 'PAS1157216' | 'Cora Red' |
|---|---|---|
| 2. STEM: | | |
| Profile: 1 = Straight; 2 = Zig-Zag | 1 | 1 |
| Branching Pattern: 1 = Single Stem; 2 = Few Branches; 3 = Many Branches | 3 | 3 |
| Stem Length from Base of Stem to Terminal Flower (cm) | 30 | 34 |
| Number of Internodes Below First Branch | 1 | 1 |
| Number of First Order Branches (From Main Stem) | 15 | 15 |
| Stem Anthocyanin: 1 = Absent; 2 = Along Veins Only; 3 = Solid Coloration | 1 | 1 |
| 3. FOLIAGE: | | |
| Leaf Type: 1 = Simple; 2 = Compound | 1 | 1 |
| Leaf Margin: 1 = Entire; 2 = Serrate; 3 = Other | 1 | 1 |
| Leaf Odor: 1 = None; 2 = Mild; 3 = Strong | 2 | 2 |
| Petiole Anthocyanin: 1 = Absent; 2 = Mild; 3 = Strong | 1 | 1 |
| Leaf Shape: 1 = Lanceolate; 2 = Elliptic; 3 = Obovate; 4 = Ovate | 2 | 2 |
| Leaf Width (mm) | 35 | 30 |
| Leaf Length (mm) | 91 | 86 |
| LEAF DORSAL SIDE: | | |
| Leaf Color: 1 = Light Green; 2 = Medium Green; 3 = Dark Green; 4 = Other | 3 | 3 |
| Color Chart Code | 2266C | 2266C |
| Pubescence: 1 = Absent; 2 = Light; 3 = Heavy | 2 | 2 |
| Luster: 1 = Dull; 2 = Shiny | 1 | 1 |
| LEAF VENTRAL SIDE: | | |
| Leaf Color: 1 = Light Green; 2 = Medium Green; 3 = Dark Green; 4 = Other | 3 | 3 |
| Color Chart Code | 574C | 574C |
| Pubescence: 1 = Absent; 2 = Light; 3 = Heavy | 1 | 1 |
| Luster: 1 = Dull; 2 = Shiny | 2 | 2 |
| 4. FLOWER: | | |
| Type: 1 = Single; 2 = Semi-Double; 3 = Double | 1 | 1 |
| Form: 1 = Flat; 2 = Cupped; 3 = Other | 1 | 1 |
| Shape: 1 = Round (Petals Overlap); 2 = Intermediate; 3 = Star (Petals Gapped) | 1 | 1 |
| Flower Odor: 1 = None; 2 = Mild; 3 = Strong | 2 | 2 |
| Pedicel Anthocyanin: 1 = Absent; 2 = Faint; 3 = Strong | 1 to 2 | 1 to 2 |
| Number Flowers per Plant | 41 | 32 |
| Flower Diameter (mm) | 56 | 60 |
| Orifice Size Including the Opening of the Corolla Tube (mm) | 3 | 3 |
| Petal Width At Widest Point (mm) | 32 | 33 |
| Petal Length From Outside Orifice to Outer Edge (mm) | 28 | 29 |
| 5. FLOWER COLORS: | | |
| Petal Color Chart Code | 207C | 207C |
| Orifice Color Chart Code | 603C | 603C |
| 6. SEEDS [Mature (Dry) Seeds]: | | |
| Seed Set: 1 = None; 2 = Poor; 3 = Fair; 4 = Good; 5 = Excellent | 4 | 4 |
| Seed Coat Color: 1 = White; 2 = Tan; 3 = Brown; 4 = Black; 5 = Other | 4 | 4 |
| Seed Weight (mg/1000 Seeds) | 1,802 | 2,336 |

TABLE 2

Physiological and Morphological Characteristics of Line P7998D and Hybrid 'PAS1157216'

|  | P7998D | 'PAS1157216' |
|---|---|---|
| 1. OVERALL PLANT HABIT (at flowering stage): | | |
| Species: 1 = C. roseus; 2 = Other | 1 | 1 |
| Ploidy: 1 = Haploid; 2 = Diploid; 3 = Triploid; 4 = Tetraploid | 2 | 2 |

TABLE 2-continued

Physiological and Morphological Characteristics of Line P7998D and Hybrid 'PAS1157216'

|  | P7998D | 'PAS1157216' |
|---|---|---|
| Life Cycle: 1 = Annual; 2 = Biennial; 3 = Perennial | 1 | 1 |
| Growth Habit: 1 = Dterminate; 2 = Semi-determinate; 3 = Indeterminate | 2 | 2 |
| Growth Form: 1 = Upright; 2 = Semi-prostrate; 3 = Prostrate | 1 | 1 |
| Flowering: 1 = Very Early; 2 = Early; 3 = Mid-season; 4 = Late; 5 = Continuous | 2 | 2 |
| Days from Planting to 50% Flowering | 49 | 49 |
| Length of Flowering Season in Days | until frost | until frost |
| Plant Height at Maturity (cm) | 32 | 32 |
| Plant Width at Maturity (cm) | 31 | 32 |
| Plant Height Class: 1 = Extra Dwarf; 2 = Dwarf; 3 = Semi-dwarf; 4 = Tall | 2 | 2 |
| Plant Width Class: 1 = Compact; 2 = Semi-compact; 3 = Spreading/Lax | 1 | 1 |
| 2. STEM: | | |
| Profile: 1 = Straight; 2 = Zig-Zag | 1 | 1 |
| Branching Pattern: 1 = Single Stem; 2 = Few Branches; 3 = Many Branches | 3 | 3 |
| Stem Length from Base of Stem to Terminal Flower (cm) | 30 | 30 |
| Number of Internodes Below First Branch | 1 | 1 |
| Number of First Order Branches (From Main Stem) | 14 | 15 |
| Stem Anthocyanin: 1 = Absent; 2 = Along Veins Only; 3 = Solid Coloration | 1 to faint | 1 |
| 3. FOLIAGE: | | |
| Leaf Type: 1 = Simple; 2 = Compound | 1 | 1 |
| Leaf Margin: 1 = Entire; 2 = Serrate; 3 = Other | 1 | 1 |
| Leaf Odor: 1 = None; 2 = Mild; 3 = Strong | 2 | 2 |
| Petiole Anthocyanin: 1 = Absent; 2 = Mild; 3 = Strong | 1 | 1 |
| Leaf Shape: 1 = Lanceolate; 2 = Elliptic; 3 = Obovate; 4 = Ovate | 2 | 2 |
| Leaf Width (mm) | 35 | 35 |
| Leaf Length (mm) | 90 | 91 |
| LEAF DORSAL SIDE: | | |
| Leaf Color: 1 = Light Green; 2 = Medium Green; 3 = Dark Green; 4 = Other | 3 | 3 |
| Color Chart Code | 2266C | 2266C |
| Pubescence: 1 = Absent; 2 = Light; 3 = Heavy | 2 | 2 |
| Luster: 1 = Dull; 2 = Shiny | 1 | 1 |
| LEAF VENTRAL SIDE: | | |
| Leaf Color: 1 = Light Green; 2 = Medium Green; 3 = Dark Green; 4 = Other | 3 | 3 |
| Color Chart Code | 574C | 574C |
| Pubescence: 1 = Absent; 2 = Light; 3 = Heavy | 1 | 1 |
| Luster: 1 = Dull; 2 = Shiny | 2 | 2 |
| 4. FLOWER: | | |
| Type: 1 = Single; 2 = Semi-Double; 3 = Double | 1 | 1 |
| Form: 1 = Flat; 2 = Cupped; 3 = Other | 1 | 1 |
| Shape: 1 = Round (Petals Overlap); 2 = Intermediate; 3 = Star (Petals Gapped) | 1 | 1 |
| Flower Odor: 1 = None; 2 = Mild; 3 = Strong | 2 | 2 |
| Pedicel Anthocyanin: 1 = Absent; 2 = Faint; 3 = Strong | 1 to 2 | 1 to 2 |
| Number Flowers per Plant | 40 | 41 |
| Flower Diameter (mm) | 49 56 if fertile | 56 |
| Orifice Size Including the Opening of the Corolla Tube (mm) | 3 | 3 |
| Petal Width At Widest Point (mm) | 28 31 if fertile | 32 |
| Petal Length From Outside Orifice to Outer Edge (mm) | 25 28 if fertile | 28 |
| 5. FLOWER COLORS: | | |
| Petal Color Chart Code | 207C | 207C |
| Orifice Color Chart Code | 603C | 603C |
| 6. SEEDS [Mature (Dry) Seeds]: | | |
| Seed Set: 1 = None; 2 = Poor; 3 = Fair; 4 = Good; 5 = Excellent | 4 | 4 |

TABLE 2-continued

Physiological and Morphological Characteristics of Line P7998D and Hybrid 'PAS1157216'

| | P7998D | 'PAS1157216' |
|---|---|---|
| Seed Coat Color: 1 = White; 2 = Tan; 3 = Brown; 4 = Black; 5 = Other | 4 | 4 |
| Seed Weight (mg/1000 Seeds) | 1,938 | 1,802 |

Example 5

Distinguishing Characteristics of Hybrid 'PAS1157216' and Parent Inbred Line P7998D The closest commercial comparison for *Catharanthus* hybrid variety 'PAS1157216' of the present invention is believed to be 'Cora Red'. In addition, hybrid 'PAS1157216' can be distinguished from its female parent, inbred line P7998D (Table 2). Distinguishing characteristics were evaluated in both a greenhouse trial grown in Guadalupe, Calif., and a field trial grown in Elburn, Ill.

For the Guadalupe, Calif. trial, plants were produced from seed and grown in a glass-covered greenhouse under conditions comparable to those used in commercial practice. The plants were grown utilizing a soilless growth medium in one-gallon containers for 15 weeks. Greenhouse temperatures were maintained at approximately 75° F. to 85° F. (24° C. to 30° C.) during the day and approximately 65° F. to 68° F. (18° C. to 20° C.) during the night. No supplemental lighting was provided.

In comparison, the plants from the Elburn, Ill. trial were produced from seed and grown in a glass-covered greenhouse under conditions comparable to those used in commercial practice using trays having growing cells measuring 2⅜×2⅜ inches and a soilless growth medium. Plants were transplanted to the field in early summer. Data was collected after 11 weeks of outdoor growth.

As shown in Table 3, 'Cora Red' is significantly taller than hybrid 'PAS1157216'. Table 4 demonstrates that hybrid 'PAS1157216' has flowers with significantly larger diameters than the male-sterile plants of inbred line P7998D.

Example 6

Origin and Breeding History of *Catharanthus* Hybrid PAS1197791'

*Catharanthus* hybrid 'PAS1197791' originated from a cross made in a greenhouse located in Guadalupe, Calif. Ball Horticultural Company proprietary inbred line P6485D previously described was used as the female parent and Ball Horticultural Company proprietary inbred line G6625D was used as the male parent. Hybrid 'PAS1197791' was trialed in California, Illinois, and Florida, and evaluated for desired horticultural characteristics, including habit and flower color at all the above trial locations, all of which were found to be uniform and stable.

A small production test was conducted in Guatemala to evaluate seed yield and seed quality of the hybrid. Seed from this production test was sent to research stations in California, Illinois, and Florida for evaluation. A larger production test was conducted in Guatemala to evaluate seed yield and quality of the hybrid. Seed from the production test was sent to research stations in California, Illinois, and Florida. The hybrid was designated 'PAS1197791' and has shown uniformity and stability, as described in the variety description information. Physiological and morphological characteristics for hybrid 'PAS1197791' and parent line P6485D are provided in Tables 5 and 6, respectively.

TABLE 3

Plant height difference between Hybrid 'PAS1157216' and 'Cora Red'

| Trial | 'PAS1157216' Average Plant Height (cm) | 'Cora Red' Average Plant Height (cm) | Sample Size Each Variety | t Critical $\alpha = .05$ | t Statistic | P Value |
|---|---|---|---|---|---|---|
| Field Trial | 31.8 +/− 3.5 | 35.3 +/− 2.3 | 10 | 2.1 | −2.6 | 1.7E−02 |
| Greenhouse Trial | 32.2 +/− 1.7 | 36.5 +/− 1.8 | 10 'PAS1157216' 9 Cora Red | 2.1 | −5.2 | 6.6E−05 |

TABLE 4

Flower diameter difference between Hybrid 'PAS1157216' and P7998D male-sterile plants

| Trial | 'PAS1157216' Average Flower Diameter (mm) | P7998D Average Flower Diameter (mm) | Sample Size Each Variety | t Critical $\alpha = .05$ | t Statistic | P Value |
|---|---|---|---|---|---|---|
| Field Trial | 45.3 +/− 2.3 | 30.5 +/− 3.5 | 15 | 2.0 | 13.7 | 6.6E−14 |
| Greenhouse Trial | 56.3 +/− 1.3 | 48.9 +/− 2.6 | 10 | 2.1 | 7.9 | 2.9E−07 |

TABLE 5

Physiological and Morphological Characteristics of Hybrid 'PAS1197791'

| | 'PAS1197791' | 'Titan Dark Red' |
|---|---|---|
| 1. OVERALL PLANT HABIT (at flowering stage): | | |
| Species: 1 = *C. roseus*; 2 = Other | 1 | 1 |
| Ploidy: 1 = Haploid; 2 = Diploid; 3 = Triploid; 4 = Tetraploid | 2 | 2 |
| Life Cycle: 1 = Annual; 2 = Biennial; 3 = Perennial | 1 | 1 |
| Growth Habit: 1 = Determinate; 2 = Semi-determinate; 3 = Indeterminate | 2 | 2 |
| Growth Form: 1 = Upright; 2 = Semi-prostrate; 3 = Prostrate | 1 | 1 |
| Flowering: 1 = Very Early; 2 = Early; 3 = Mid-season; 4 = Late; 5 = Continuous | 2 | 2 |
| Days from Planting to 50% Flowering | 49 | 50 |
| Length of Flowering Season in Days | until frost | until frost |
| Plant Height at Maturity (cm) | 31 | 32 |
| Plant Width at Maturity (cm) | 30 | 30 |
| Plant Height Class: 1 = Extra Dwarf; 2 = Dwarf; 3 = Semi-dwarf; 4 = Tall | 2 | 2 |
| Plant Width Class: 1 = Compact; 2 = Semi-compact; 3 = Spreading/Lax | 1 | 1 |
| 2. STEM: | | |
| Profile: 1 = Straight; 2 = Zig-Zag | 1 | 1 |
| Branching Pattern: 1 = Single Stem; 2 = Few Branches; 3 = Many Branches | 3 | 3 |
| Stem Length from Base of Stem to Terminal Flower (cm) | 29 | 30 |
| Number of Internodes Below First Branch | 1 | 1 |
| Number of First Order Branches (From Main Stem) | 14 | 14 |
| Stem Anthocyanin: 1 = Absent; 2 = Along Veins Only; 3 = Solid Coloration | 1 to faint | 1 to faint |
| 3. FOLIAGE: | | |
| Leaf Type: 1 = Simple; 2 = Compound | 1 | 1 |
| Leaf Margin: 1 = Entire; 2 = Serrate; 3 = Other | 1 | 1 |
| Leaf Odor: 1 = None; 2 = Mild; 3 = Strong | 2 | 2 |
| Petiole Anthocyanin: 1 = Absent; 2 = Mild; 3 = Strong | 1 to faint | 1 |
| Leaf Shape: 1 = Lanceolate; 2 = Elliptic; 3 = Obovate; 4 = Ovate | 2 | 2 |
| Leaf Width (mm) | 35 | 35 |
| Leaf Length (mm) | 95 | 101 |
| LEAF DORSAL SIDE: | | |
| Leaf Color: 1 = Light Green; 2 = Medium Green; 3 = Dark Green; 4 = Other | 3 | 3 |
| Color Chart Code | 2266C | 2266C |
| Pubescence: 1 = Absent; 2 = Light; 3 = Heavy | 2 | 2 |
| Luster: 1 = Dull; 2 = Shiny | 1 | 1 |
| LEAF VENTRAL SIDE: | | |
| Leaf Color: 1 = Light Green; 2 = Medium Green; 3 = Dark Green; 4 = Other | 3 | 3 |
| Color Chart Code | 574C | 574C |
| Pubescence: 1 = Absent; 2 = Light; 3 = Heavy | 1 | 1 |
| Luster: 1 = Dull; 2 = Shiny | 2 | 2 |
| 4. FLOWER: | | |
| Type: 1 = Single; 2 = Semi-Double; 3 = Double | 1 | 1 |
| Form: 1 = Flat; 2 = Cupped; 3 = Other | 1 | 1 |
| Shape: 1 = Round (Petals Overlap); 2 = Intermediate; 3 = Star (Petals Gapped) | 1 | 1 |
| Flower Odor: 1 = None; 2 = Mild; 3 = Strong | 2 | 2 |
| Pedicel Anthocyanin: 1 = Absent; 2 = Faint; 3 = Strong | 1 to 2 | 1 |
| Number Flowers per Plant | 28 | 34 |
| Flower Diameter (mm) | 55 | 58 |
| Orifice Size Including the Opening of the Corolla Tube (mm) | 3 | 3 |
| Petal Width At Widest Point (mm) | 33 | 32 |
| Petal Length From Outside Orifice to Outer Edge (mm) | 28 | 29 |
| 5. FLOWER COLORS: | | |
| Petal Color Chart Code | 206C | 206C |
| Orifice Color Chart Code | 208C | 208C |
| 6. SEEDS [Mature (Dry) Seeds]: | | |
| Seed Set: 1 = None; 2 = Poor; 3 = Fair; 4 = Good; 5 = Excellent | 4 | 4 |

TABLE 5-continued

Physiological and Morphological Characteristics of Hybrid 'PAS1197791'

|  | 'PAS1197791' | 'Titan Dark Red' |
|---|---|---|
| Seed Coat Color: 1 = White; 2 = Tan; 3 = Brown; 4 = Black; 5 = Other | 4 | 4 |
| Seed Weight (mg/1000 Seeds) | 1,802 | 1,786 |

TABLE 6

Physiological and Morphological Characteristics of Line P6485D and Hybrid 'PAS1197791'

|  | P6485D | 'PAS1197791' |
|---|---|---|
| 1. OVERALL PLANT HABIT (at flowering stage): | | |
| Species: 1 = *C. roseus*; 2 = Other | 1 | 1 |
| Ploidy: 1 = Haploid; 2 = Diploid; 3 = Triploid; 4 = Tetraploid | 2 | 2 |
| Life Cycle: 1 = Annual; 2 = Biennial; 3 = Perennial | 1 | 1 |
| Growth Habit: 1 = Determinate; 2 = Semi-determinate; 3 = Indeterminate | 2 | 2 |
| Growth Form: 1 = Upright; 2 = Semi-prostrate; 3 = Prostrate | 1 | 1 |
| Flowering: 1 = Very Early; 2 = Early; 3 = Mid-season; 4 = Late; 5 = Continuous | 2 | 2 |
| Days from Planting to 50% Flowering | 50 | 49 |
| Length of Flowering Season in Days | until frost | until frost |
| Plant Height at Maturity (cm) | 30 | 31 |
| Plant Width at Maturity (cm) | 30 | 30 |
| Plant Height Class: 1 = Extra Dwarf; 2 = Dwarf; 3 = Semi-dwarf; 4 = Tall | 2 | 2 |
| Plant Width Class: 1 = Compact; 2 = Semi-compact; 3 = Spreading/Lax | 1 | 1 |
| 2. STEM: | | |
| Profile: 1 = Straight; 2 = Zig-Zag | 1 | 1 |
| Branching Pattern: 1 = Single Stem; 2 = Few Branches; 3 = Many Branches | 3 | 3 |
| Stem Length from Base of Stem to Terminal Flower (cm) | 27 | 29 |
| Number of Internodes Below First Branch | 1 | 1 |
| Number of First Order Branches (From Main Stem) | 14 | 14 |
| Stem Anthocyanin: 1 = Absent; 2 = Along Veins Only; 3 = Solid Coloration | 1 to faint | 1 to faint |
| 3. FOLIAGE: | | |
| Leaf Type: 1 = Simple; 2 = Compound | 1 | 1 |
| Leaf Margin: 1 = Entire; 2 = Serrate; 3 = Other | 1 | 1 |
| Leaf Odor: 1 = None; 2 = Mild; 3 = Strong | 2 | 2 |
| Petiole Anthocyanin: 1 = Absent; 2 = Mild; 3 = Strong | 1 | 1 to faint |
| Leaf Shape: 1 = Lanceolate; 2 = Elliptic; 3 = Obovate; 4 = Ovate | 2 | 2 |
| Leaf Width (mm) | 35 | 35 |
| Leaf Length (mm) | 94 | 95 |
| LEAF DORSAL SIDE: | | |
| Leaf Color: 1 = Light Green; 2 = Medium Green; 3 = Dark Green; 4 = Other | 3 | 3 |
| Color Chart Code | 2266C | 2266C |
| Pubescence: 1 = Absent; 2 = Light; 3 = Heavy | 2 | 2 |
| Luster: 1 = Dull; 2 = Shiny | 1 | 1 |
| LEAF VENTRAL SIDE: | | |
| Leaf Color: 1 = Light Green; 2 = Medium Green; 3 = Dark Green; 4 = Other | 3 | 3 |
| Color Chart Code | 574C | 574C |
| Pubescence: 1 = Absent; 2 = Light; 3 = Heavy | 1 | 1 |
| Luster: 1 = Dull; 2 = Shiny | 2 | 2 |
| 4. FLOWER: | | |
| Type: 1 = Single; 2 = Semi-Double; 3 = Double | 1 | 1 |
| Form: 1 = Flat; 2 = Cupped; 3 = Other | 1 | 1 |
| Shape: 1 = Round (Petals Overlap); 2 = Intermediate; 3 = Star (Petals Gapped) | 1 | 1 |
| Flower Odor: 1 = None; 2 = Mild; 3 = Strong | 2 | 2 |
| Pedicel Anthocyanin: 1 = Absent; 2 = Faint; 3 = Strong | 1 | 1 to faint |
| Number Flowers per Plant | 23 | 28 |

TABLE 6-continued

Physiological and Morphological Characteristics of Line P6485D and Hybrid 'PAS1197791'

|  | P6485D | 'PAS1197791' |
|---|---|---|
| Flower Diameter (mm) | 51 | 55 |
|  | 56 if fertile |  |
| Orifice Size Including the Opening of the Corolla Tube (mm) | 3 | 3 |
| Petal Width At Widest Point (mm) | 31 | 33 |
|  | 33 if fertile |  |
| Petal Length From Outside Orifice to Outer Edge (mm) | 25 | 28 |
|  | 27 if fertile |  |
| 5. FLOWER COLORS: |  |  |
| Petal Color Chart Code | 205C | 206C |
| Orifice Color Chart Code | 208C | 208C |
| 6. SEEDS [Mature (Dry) Seeds]: |  |  |
| Seed Set: 1 = None; 2 = Poor; 3 = Fair; 4 = Good; 5 = Excellent | 4 | 4 |
| Seed Coat Color: 1 = White; 2 = Tan; 3 = Brown; 4 = Black; 5 = Other | 4 | 4 |
| Seed Weight (mg/1000 Seeds) | 1,828 | 1,802 |

Example 7

Distinguishing Characteristics of Hybrid 'PAS1197791' and Inbred Line P6485D

The closest commercial comparison for hybrid 'PAS1197791' of the present invention is believed to be 'Titan Dark Red', which is produced as a traditional hybrid rather than through use of a male-sterile female and thus does not have a male-sterile allele. In addition, hybrid 'PAS1197791' can be distinguished from its female parent, inbred line P6485D. Distinguishing characteristics were evaluated in both a greenhouse trial grown in Guadalupe, Calif., and a field trial grown in Elburn, Ill.

For the Guadalupe, Calif. trial, plants were produced from seed and grown in a glass-covered greenhouse under conditions comparable to those used in commercial practice. The plants were grown utilizing a soilless growth medium in one-gallon containers for 15 weeks. Greenhouse temperatures were maintained at approximately 75° F. to 85° F. (24° C. to 30° C.) during the day and approximately 65° F. to 68° F. (18° C. to 20° C.) during the night. No supplemental lighting was provided.

In comparison, the plants from the Elburn, Ill. trial plants were produced from seed and grown in a glass-covered greenhouse under conditions comparable to those used in commercial practice using trays having growing cells measuring 2⅜×2⅜ inches and a soilless growth medium. Plants were transplanted to the field in early summer. Data was collected after 11 weeks of outdoor growth.

Table 7 illustrates that 'PAS1197791' has significantly larger diameter flowers than male-sterile plants of inbred line P6485D. In addition, as shown in Table 6, hybrid 'PAS1197791' has slightly darker red-colored flowers than line P6485D.

TABLE 7

Flower diameter difference between Hybrid 'PAS1197791' and P6485D male-sterile plants

| Trial | 'PAS1197791' Average Flower Diameter (mm) | P6485D Average Flower Diameter (mm) | Sample Size Each Variety | t Critical α = .05 | t Statistic | P Value |
|---|---|---|---|---|---|---|
| Field Trial | 46.4 +/− 2.0 | 32.3 +/− 3.1 | 15 | 2.0 | 14.8 | 9.5E−15 |
| Greenhouse Trial | 54.7 +/− 2.1 | 50.1 +/− 2.2 | 10 | 2.1 | 4.8 | 1.5E−04 |

Example 8

Origin and Breeding History of *Catharanthus* Male Inbred Line G6625D

Inbred line G6625D was developed using the pedigree breeding system. The original developmental cross was made in the greenhouses in Guadalupe, Calif. using Ball Horticultural company proprietary inbred line 00-1496 as the female parent and Ball Horticultural company proprietary inbred line 00-1540 as the male parent.

The F1 seed resulting from this cross was sown in a greenhouse, and the plants were massed to produce F2 seed. The F2 seed was grown and the plants evaluated, and single plant selections were made for general horticultural characteristics, including a well-branched habit, early flowering, large, dark red-colored flowers with light-colored orifice, and overlapping petals.

Several F3 families were selected for the above characteristics along with additional selection of uniformity for flower color. All progeny was advanced by single plant selections. Subsequent F4 to F6 generations were advanced while continuing to select for the above characteristics. An F6 family was selected and massed to produce breeder's seed. The massed seed was used make stock seed.

The plants massed were shown to be stable. No variations or off-types were observed in either the breeder's seed increase or the stock seed increase. The inbred line was designated G6625D and was stable for two generations of seed increase, which include the breeder's seed increase and the stock seed increase.

Example 9

CAPS and HRM Markers to Differentiates *Catharanthus roseus* Accessions

Total DNA isolated from the cotyledons of *Catharanthus roseus* accessions 'Titan Dark Red', 'PAS1197791', 3Vin1496-00, P6485D, and G6625D was subjected to end-point PCR using the inter-simple sequence repeat (ISSR) primer #807 (5'-AGAGAGAGAGAGAGAGT-3', SEQ ID NO:1) of the University of British Columbia (UBC) ISSR Primer Set. The amplicons were electrophoresed on a 1.8% high-resolution agarose gel and visualized with EZ-Vision dye on a UV transilluminator. Inspection of the genetic fingerprints revealed that the male-sterile female, P6485D, was missing a ~850-bp DNA fragment that was present in the other accessions. This suggested that a DNA polymorphism existed in this accession that could be used to differentiate 'Titan Dark Red' and 'PAS1197791' at the genetic level.

This 850-bp fragment was cloned from 3Vin1496-00 into plasmid pCR4-TOPO and then subjected to DNA sequence analysis. The nucleotide sequence was subsequently submitted for BLAST analysis to the *C. roseus* 'Sunset Apricot' genomic sequences located on the Medicinal Plant Genomics Resource website at medicinalplantgenomics.msu.edu/. *C. roseus* scaffold 3064404 was identified as harboring the sequence with the highest homology (95%) to this amplicon. Using the 3064404 scaffold sequence, two primer pairs were designed and synthesized to amplify fragments from this region of the *C. roseus* genome. The primers were as follows:

3064404-5' (5'-GATGGATAATGAGATAATTGGGC-3', SEQ ID NO:2) and 3064404-3' (5'-GACCAAAT-TCATAAATGAGTGATATCC-3') amplified a fragment of approximately 440 bp.

3064404-5'-2 (5'-GATCAGATACCCAAGAGCATTG-3', SEQ ID NO:3) and 3064404-3'-2 (5'-GTAGG-TAAGGAAGTGTGTGAGGAC-3', SEQ ID NO:4) amplified a fragment of approximately 975 bp.

Amplicons of these lengths were generated from DNA of 3Vin1496-00, P6485D, and G6625D, and subjected to DNA sequence analysis. A comparison of the DNA sequences from these two female inbred parents and the single male inbred parent revealed the presence of numerous SNPs between P6485D and the other parental lines, some of which either destroyed or created restriction sites which could be useful for CAPS marker analysis.

The ~440-bp amplicon synthesized with primers 3064404-5' and 3064404-3' was digested with the restriction enzyme, AluI. It was predicted and confirmed that a single diagnostic AluI restriction fragment of ~400-bp was shared between 'Titan Dark Red' and its two parents, 3Vin1496-00 and G6625D (the smaller ~40-bp fragment could not be visualized on this gel system) (FIG. 1). In contrast, a diagnostic AluI restriction fragment of ~365-bp was expected and observed in P6485D due to the creation of a new AluI restriction site in its genomic sequence. Thus, 'PAS1197791' was anticipated to contain both diagnostic AluI restriction fragments, ~400-bp (G6625D-derived) and ~365-bp (P6485D-derived), respectively. This restriction digest pattern was observed in 'PAS1197791' which allowed easy differentiation of the two hybrids, 'Titan Dark Red' and 'PAS1197791'.

Similarly, the ~975-bp amplicon synthesized with primer pair 3064404-5'-2/3064404-3'-2 was digested with either BstNI or TaqaI. In the case of the BstNI restriction digest, the genomic fragment from P6485D lacks any BstNI restriction sites and will represent the full-length amplicon. In comparison, 'Titan Dark Red' and its parents (3Vin1496-00 and G6625D) contain a single BstNI restriction site, yielding two (~575-bp/~400-bp) diagnostic BstNI restriction fragments. It was predicted and observed that 'PAS1197791' would display a prominent ~975-bp fragment (derived from P6485D), along with the two smaller restriction fragments originating from G6625D.

Regarding the TaqaI restriction digest patterns, 'Titan Dark Red' and its two parents (3Vin1496-00 and G6625D) were predicted to display two restriction digest fragments of ~550-bp and ~380-bp (a 45-bp fragment is difficult to observe). While the ~380-bp fragment was evident, the ~550-bp fragment was slightly smaller than expected, which might be due to inadvertent cutting caused by "star activity," sometimes associated with this restriction enzyme. In contrast, the P6485D-derived amplicon has lost one of the TaqaI restriction sites and was expected to display ~550-bp and ~425-bp fragments. As predicted, 'PAS1197791' displayed all four TaqaI restriction fragments, two each originating from P6485D and G6625D. Taken together, these results support the conclusion that 'Titan Dark Red' and 'PAS1197791' can be differentiated using these three CAPS markers (AluI, BstNI and TaqaI).

Figure 2:
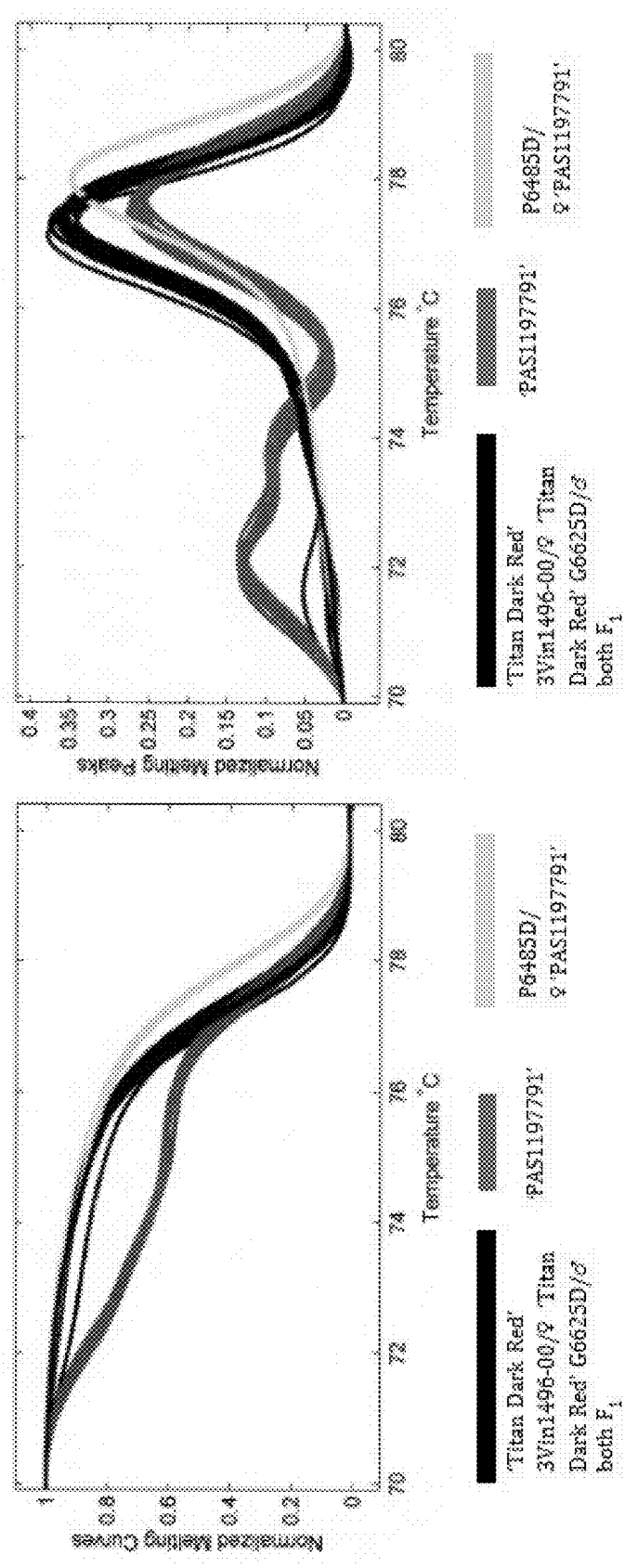
FIG. 2—Shows high-resolution melting marker assays to differentiate *Vinca* varieties 'Titan Dark Red' and 'PAS1197791'.

To expand the study further, an additional 11 'Titan Dark Red' and 15 'PAS1197791' seedlings were analyzed for the presence of two new neighboring SNPs. The primers, 3064404 HRM-5' (5'-AATGTTAAGTAGCTGCGT-GTCTC-3', SEQ ID NO:5) and 3064404 HRM-3' (5'-CCTATAAATTCTATAACTGCTCGTCTTTC-3', SEQ ID NO:6) generated SNP-containing amplicons that could be differentiated via high-resolution DNA melting analysis (FIG. 2). As expected, 'Titan Dark Red', and its two parents, 3Vin1496-00 and G6625D, shared the same DNA melting profile, since no SNPs are present among these three accessions. However, the male-sterile female parent, P6485D, displayed an alternate DNA melting profile due to the presence of two neighboring nucleotides that differed from the 'Titan Dark Red'-related lines. Finally, as expected, 'PAS1197791'-derived amplicons displayed a more complex DNA melting profile due to the heterozygosity that exists at these two SNP locations in the F1 hybrid seedlings. Taken together with the CAPS marker assay results, five SNPs have been identified that can be utilized to differentiate the two F1 hybrids, 'Titan Dark Red' and 'PAS1197791'.

What is claimed is:

1. A *Catharanthus roseus* plant comprising a nuclear recessive allele, wherein the nuclear recessive allele confers male-sterility, wherein *Catharanthus roseus* line P7998D comprises the nuclear recessive allele, and wherein representative seed of *Catharanthus roseus* line P7998D has been deposited under ATCC Accession No. PTA-122493.

2. The plant of claim 1, wherein the plant is homozygous for the allele.

3. The plant of claim 1, wherein the plant is heterozygous for the allele.

4. The plant of claim 1, wherein the plant is hybrid.

5. The plant of claim 1, wherein the plant is inbred.

6. The plant of claim 1, wherein the plant comprises a transgene.

7. The plant of claim 1, wherein the plant comprises a single locus conversion.

8. A plant part comprising a cell of the plant of claim 1.

9. The plant part of claim 8, further defined as a cutting, a leaf, pollen, an ovule, or a flower.

10. A seed that produces the plant of claim 1.

11. A seed produced from the plant of claim 1, wherein the seed comprises said nuclear recessive allele.

12. The seed of claim 11, which is inbred.

13. The seed of claim 11, which is hybrid.

14. A tissue culture of regenerable cells of the plant of claim 1.

15. The tissue culture according to claim 14, comprising cells or protoplasts from a plant part selected from the group consisting of embryos, meristems, cotyledons, pollen, leaves, anthers, roots, root tips, pistil, flower, seed, stems, and protoplasts or callus derived therefrom;
    wherein at least one cell of said tissue culture comprises said nuclear recessive allele.

16. A plant regenerated from the tissue culture of claim 14, wherein the regenerated plant comprises the male sterility allele.

17. A method of introducing a desired trait into a *Catharanthus roseus* plant, comprising:
    (a) crossing a plant according to claim 1 with a second, distinct *Catharanthus roseus* plant that comprises a desired trait to produce F1 progeny;
    (b) selecting an F1 progeny that comprises the desired trait;
    (c) crossing the selected F1 progeny with a *Catharanthus roseus* plant that is homozygous for said nuclear recessive allele to produce second generation progeny; and
    (d) repeating steps (c) and (d) three or more times in succession to produce fifth or higher generation progeny that comprise the desired trait.

18. A plant produced by the method of claim 17, wherein the plant comprises said male sterility allele.

19. A method of producing a *Catharanthus roseus* plant comprising an added desired trait, the method comprising: introducing a transgene or single locus conversion conferring the desired trait into a plant according to claim 1.

20. A method for producing hybrid *Catharanthus roseus* seed comprising the steps of:
    (a) crossing a first plant according to claim 2 with a second, distinct *Catharanthus roseus* plant capable of being crossed thereto; and
    (b) collecting resulting seed.

21. The method of claim 20, further comprising the steps of:
    (c) crossing a plant grown from said seed of step (b) with itself or a different *Catharanthus roseus* plant at least one additional time to yield additional seed.

22. The method of claim 20, wherein the first plant is a plant of *Catharanthus* line P7998D.

23. A method of producing a *Catharanthus roseus* plant with an allele that confers male sterility, said method comprising: introgressing the allele from a plant according to claim 1 into a *Catharanthus roseus* plant of a different genotype.

24. An F1 hybrid seed, wherein the seed is produced by crossing a first plant according to claim 1 with a second, distinct *Catharanthus roseus* plant, wherein the seed comprises said nuclear recessive allele.

25. The F1 hybrid seed of claim 24, wherein said first plant is a female parent.

26. A plant produced by growing the seed of claim 25, wherein the plant comprises the allele.

27. A plant part comprising a cell of the plant of claim 26, wherein said cell comprises the allele.

28. The plant part of claim 27, further defined as a cutting, leaf, an ovule, pollen, or a flower.

29. A method of vegetatively propagating the plant of claim 1, comprising the steps of:
    (a) collecting tissue capable of being propagated from a plant according to claim 1;
    (b) cultivating said tissue to obtain proliferated shoots; and
    (c) rooting said proliferated shoots to obtain rooted plantlets.

30. The method of claim 29, further comprising growing at least a first plant from said rooted plantlets.

31. A hybrid *Catharanthus roseus* plant comprising a nuclear recessive allele, obtainable by crossing a *Catharanthus roseus* plant comprising said allele, with a second *Catharanthus roseus* plant lacking said allele, wherein said allele confers male-sterility, wherein *Catharanthus roseus* line P7998D comprises said allele, and wherein representative seed of *Catharanthus roseus* line P7998D has been deposited under ATCC Accession No. PTA-122493.

\* \* \* \* \*

SEQUENCE LISTING

<160> NUMBER OF SEQ ID NOS: 6

<210> SEQ ID NO 1
<211> LENGTH: 17
<212> TYPE: DNA

```
<213> ORGANISM: Artificial Sequence
<220> FEATURE:
<223> OTHER INFORMATION: Primer

<400> SEQUENCE: 1
agagagagag agagagt                                                    17

<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2
gatggataat gagataattg ggc                                             23

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
gatcagatac ccaagagcat tg                                              22

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
gtaggtaagg aagtgtgtga ggac                                            24

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
aatgttaagt agctgcgtgt ctc                                             23

<210> SEQ ID NO 6
<211> LENGTH: 29
<212> TYPE: DNA
<213> ORGANISM: Artificial Sequence
<220> FEATURE:
<223> OTHER INFORMATION: Primer

<400> SEQUENCE: 6
cctataaatt ctataactgc tcgtctttc                                       29
```